United States Patent
Halpert et al.

(10) Patent No.: US 11,696,985 B2
(45) Date of Patent: Jul. 11, 2023

(54) FLUID THERAPY METHOD

(71) Applicant: Reprieve Cardiovascular, Inc., Milford, MA (US)

(72) Inventors: Andrew V. Halpert, Brookline, MA (US); Mark Tauscher, Medfield, MA (US); Mark Gelfand, New York, NY (US); Howard Levin, Teaneck, NJ (US)

(73) Assignee: Reprieve Cardiovascular, Inc., Milford, MA (US)

( * ) Notice: Subject to any disclaimer, the term of this patent is extended or adjusted under 35 U.S.C. 154(b) by 676 days.

(21) Appl. No.: 16/863,824

(22) Filed: Apr. 30, 2020

(65) Prior Publication Data
US 2020/0254178 A1    Aug. 13, 2020

Related U.S. Application Data

(63) Continuation of application No. 16/032,453, filed on Jul. 11, 2018, now Pat. No. 10,639,419, which is a
(Continued)

(51) Int. Cl.
*A61M 31/00*    (2006.01)
*A61M 5/172*    (2006.01)

(52) U.S. Cl.
CPC ... *A61M 5/1723* (2013.01); *A61M 2202/0496* (2013.01); *A61M 2230/005* (2013.01)

(58) Field of Classification Search
CPC .......... A61M 2205/3393; A61M 5/142; A61M 5/16895; A61M 5/1723; A61M 2230/005;
(Continued)

(56) References Cited

U.S. PATENT DOCUMENTS

| | | | |
|---|---|---|---|
| 3,954,010 A | 5/1976 | Hilblom | |
| 4,132,644 A | 1/1979 | Kolberg | |

(Continued)

FOREIGN PATENT DOCUMENTS

| | | |
|---|---|---|
| EP | 0258690 | 3/1988 |
| JP | 2008/110150 | 5/2008 |

(Continued)

OTHER PUBLICATIONS

Urexact® 2000 System, mhtml:file//C:\Documents%20and%20Settings\bob\Local%20Settings\Temporary%20Intt . . . (Jul. 22, 2005) (three (3) pages).

(Continued)

*Primary Examiner* — Rebecca E Eisenberg
(74) *Attorney, Agent, or Firm* — Perkins Coie LLP

(57) ABSTRACT

A fluid therapy method for an ADHF patient includes setting a urine output rate desired threshold, setting one or more desired negative net gain rates, and optionally setting a total fluid loss goal. The urine output of the patient is monitored and fluid is automatically administered to the patient at increasing rates to equal to or approximately match the patient's increasing urine output rates until the patient's urine output rate reaches the set urine output rate desired threshold. Thereafter, fluid is administered to the patient at rates to achieve the set desired negative net gain rate until the fluid loss goal is reached. Thereafter, until the end of therapy, fluid is administered to the patient at rates equal to or approximately equal to the monitored urine output rates.

19 Claims, 5 Drawing Sheets

Related U.S. Application Data continuation of application No. 14/645,730, filed on Mar. 12, 2015, now abandoned.

(60) Provisional application No. 61/954,089, filed on Mar. 17, 2014.

(58) Field of Classification Search
CPC .......... A61M 2202/0496; G01G 17/04; A61B 5/201; A61B 5/208; A61B 5/20
See application file for complete search history.

(56) References Cited

U.S. PATENT DOCUMENTS

| | | | |
|---|---|---|---|
| 4,146,029 A | 3/1979 | Ellinwood, Jr. | |
| 4,204,957 A | 5/1980 | Weickhardt | |
| 4,216,462 A | 8/1980 | McGrath et al. | |
| 4,229,299 A | 10/1980 | Savitz et al. | |
| 4,261,360 A | 4/1981 | Perez | |
| 4,275,726 A | 6/1981 | Schael | |
| 4,291,692 A | 9/1981 | Bowman et al. | |
| 4,343,316 A | 8/1982 | Jespersen | |
| 4,448,207 A | 5/1984 | Parrish | |
| 4,449,538 A | 5/1984 | Corbitt et al. | |
| 4,504,263 A | 3/1985 | Steuer et al. | |
| 4,658,834 A | 4/1987 | Blankenship et al. | |
| 4,712,567 A | 12/1987 | Gille et al. | |
| 4,728,433 A | 3/1988 | Buck et al. | |
| 4,813,925 A | 3/1989 | Anderson, Jr. et al. | |
| 4,923,598 A | 5/1990 | Schal | |
| 4,994,026 A | 2/1991 | Fecondini | |
| 5,098,379 A | 3/1992 | Conway et al. | |
| 5,176,148 A | 1/1993 | Weist et al. | |
| 5,207,642 A | 5/1993 | Orkin et al. | |
| 5,573,506 A | 11/1996 | Vasko | |
| 5,722,947 A | 3/1998 | Jeppsson et al. | |
| 5,769,087 A | 6/1998 | Westphal et al. | |
| 5,814,009 A | 9/1998 | Wheatman | |
| 5,891,051 A | 4/1999 | Han et al. | |
| 5,910,252 A | 6/1999 | Truitt et al. | |
| 5,916,153 A | 6/1999 | Rhea, Jr. | |
| 5,916,195 A | 6/1999 | Eshel et al. | |
| 5,981,051 A | 11/1999 | Motegi et al. | |
| 6,010,454 A | 1/2000 | Arieff et al. | |
| 6,171,253 B1 | 1/2001 | Bullister et al. | |
| 6,231,551 B1 | 5/2001 | Barbut | |
| 6,272,930 B1 | 8/2001 | Crozafon et al. | |
| 6,514,226 B1 | 2/2003 | Levin et al. | |
| 6,531,551 B2 | 3/2003 | Levin et al. | |
| 6,537,244 B2 | 3/2003 | Paukovits et al. | |
| 6,554,791 B1 | 4/2003 | Cartledge et al. | |
| 6,640,649 B1 | 11/2003 | Paz et al. | |
| 6,740,072 B2 | 5/2004 | Starkweather | |
| 6,752,779 B2 | 6/2004 | Paukovits et al. | |
| 6,796,960 B2 | 9/2004 | Cioanta et al. | |
| 6,827,702 B2 | 12/2004 | Lebel et al. | |
| 6,942,637 B2 | 9/2005 | Cartledge et al. | |
| 7,029,456 B2 | 4/2006 | Ware et al. | |
| 7,044,002 B2 | 5/2006 | Ericson et al. | |
| 7,137,964 B2 | 11/2006 | Flaherty | |
| 7,278,983 B2 | 10/2007 | Ireland et al. | |
| 7,727,222 B2 | 6/2010 | Da Silva et al. | |
| 7,736,354 B2 | 6/2010 | Gelfand et al. | |
| 7,758,562 B2 | 7/2010 | Gelfand et al. | |
| 7,758,563 B2 | 7/2010 | Gelfand et al. | |
| 7,837,667 B2 | 11/2010 | Gelfand et al. | |
| 7,938,817 B2 | 5/2011 | Gelfand et al. | |
| 8,007,460 B2 | 8/2011 | Gelfand et al. | |
| 8,075,513 B2 | 12/2011 | Rudko et al. | |
| 8,444,263 B2 | 5/2013 | Kojima | |
| 2002/0025597 A1 | 2/2002 | Matsuda | |
| 2002/0072647 A1 | 6/2002 | Schock et al. | |
| 2002/0107536 A1 | 8/2002 | Hussein | |
| 2002/0151834 A1 | 10/2002 | Utterberg | |
| 2002/0161314 A1 | 10/2002 | Sarajarvi | |
| 2003/0048185 A1 | 3/2003 | Citrebaum et al. | |
| 2003/0048432 A1 | 3/2003 | Jeng et al. | |
| 2003/0114786 A1 | 6/2003 | Hiller et al. | |
| 2004/0025597 A1 | 2/2004 | Ericson et al. | |
| 2004/0059295 A1 | 3/2004 | Cartledge et al. | |
| 2004/0081585 A1 | 4/2004 | Reid | |
| 2004/0087894 A1 | 5/2004 | Flaherty | |
| 2004/0122353 A1 | 6/2004 | Shahmirian et al. | |
| 2004/0133187 A1 | 7/2004 | Hickle | |
| 2004/0163655 A1 | 8/2004 | Gelfand et al. | |
| 2004/0167415 A1 | 8/2004 | Gelfand et al. | |
| 2004/0167464 A1 | 8/2004 | Ireland et al. | |
| 2004/0176703 A1 | 9/2004 | Christensen | |
| 2004/0193328 A1 | 9/2004 | Zaitsu et al. | |
| 2004/0243075 A1 | 12/2004 | Harvie | |
| 2005/0027254 A1 | 2/2005 | Vasko | |
| 2005/0065464 A1 | 3/2005 | Talbot et al. | |
| 2005/0085760 A1 | 4/2005 | Ware et al. | |
| 2006/0052764 A1 | 3/2006 | Gelfand et al. | |
| 2006/0064053 A1 | 3/2006 | Bollish et al. | |
| 2006/0184084 A1 | 8/2006 | Ware | |
| 2006/0235353 A1 | 10/2006 | Gelfand et al. | |
| 2006/0253064 A1 | 11/2006 | Gelfand et al. | |
| 2006/0270971 A1 | 11/2006 | Gelfand et al. | |
| 2007/0088333 A1 | 4/2007 | Levin et al. | |
| 2008/0027409 A1 | 1/2008 | Rudko et al. | |
| 2008/0033394 A1 | 2/2008 | Gelfand et al. | |
| 2008/0171966 A1 | 7/2008 | Rudko et al. | |
| 2008/0221512 A1 | 9/2008 | DaSilva | |
| 2010/0280444 A1 | 1/2010 | Gelfand et al. | |
| 2010/0234797 A1 | 9/2010 | Gelfand et al. | |
| 2010/0274217 A1 | 10/2010 | Da Silva et al. | |
| 2010/0280443 A1 | 11/2010 | Gelfand et al. | |
| 2010/0280445 A1 | 11/2010 | Gelfand et al. | |
| 2011/0046516 A1 | 2/2011 | Paz et al. | |
| 2012/0259308 A1 | 10/2012 | Gelfand et al. | |

FOREIGN PATENT DOCUMENTS

| | | |
|---|---|---|
| WO | WO 98/16685 | 6/1996 |
| WO | WO 96/28209 | 9/1996 |
| WO | WO 97/16220 | 5/1997 |
| WO | WO 99/06087 A1 | 2/1999 |
| WO | WO 2006/041496 A1 | 4/2006 |

OTHER PUBLICATIONS

Bard Lubricath 3-Way Catheters, Bard Medical Division, http://www/bardmedical.com/urology/cathtour/3way.html (Jul. 6, 2005) (one (1) page).

Foley Catheter Introduction, Foley Cathetar, http://www/wmedicinehealth.com/articles/11633-1.asp: http://www.emedicinehealth.com/articles/11633-8.asp (Jul. 6, 2005) (two (2) pages).

Gambro Acute Renal Failure, Prisma, http://www.gambro.com/Page.asp?id=2446: http://www.gambro.com/upload/press_media_toolkit/download_images/Prisma.jpg (Jul. 6, 2005) (two (2) pages.

Angiometrx, The Metricath System, http://www.angiometrx.com/Metricath%20System.htm (Jul. 6, 2005) (one (1) page).

Merit Medical Systems, Inc., 2003 Annual Report; Balloon Inflation Devices & Pressure Monitoring Syringes; Tranducers and Accessories, http://www.corporatewindow.com/annuals/mmsi03/10kpages5.html (Jul. 6, 2005) (three (3) pages).

Millar Instruments: Single Sensor Cardiology Catheters, Cardiovascular Mikro-Tip Pressure Transducer Catheters. http://www.millarinstruments.com/products/cardio/cardio_sngldual.html (Jul. 6, 2005) (five (5) pages).

Infusion Dynamics: Power Infuser, The Power Infuser, http://www.infusiondynamics.com/powerinfuser/ (Apr. 4, 2005) (two (2) pages).

S215 Ultra Low Profile Single Point Load Cell—Strain Guage Sensors and Load Calls, Ultra-Low Profile Single Point Load Cell-S215, http://smdsensors.com/detail_pgs/s215.htm (Apr. 4, 2005) (two (2) pages).

Rihal et al., Incidence and Prognostic Importance of Actue Renal Failure After Percutaneous Coronary Intervention, Circulation, May 14, 2002, pp. 2259-2254 (six (6) pages).

(56) References Cited

OTHER PUBLICATIONS

Levin et al., High-volume diuresis with matched maintenance of intravascular volume may prevent contrast-induced nephropathy in post-transplant patients with moderate-severe baseline renal impairment, Cardiovascular Revascularization Medicine, Elsevier, NL, vol. 8, No. 2, Apr. 1, 2007, p. 153 (one (1) page).
Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21 (eleven (11) pages).
Wakelkamp et al., The influence of drug input rate on the development of tolerance to frusemide, Br. J. Clin. Pharmacol 1998, 46:479-487. pp. 479-487 (nine (9) pages).
Stevens, Melsssa A., MD et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb. 1999, pp. 403-411 (nine (9) pages).
Rosamilia et al., Electromotive Drug Administration of Lidocaine and Dexamethasone Followed By Cystodistension in Women with Interstitial Cystitis, International Urogyecologyl Journal, Pelvic Floor Dysfunction 1997; 8; 142-5 (four (4) pages).
Gloor, James M. and Vincente E. Torres, Reflux and Obstructive Nephropathy, Atlas of Diseases of the Kidney, on-line edition, vol. Two, Section I, Ch. 8, pp. 8.1-8.25 (date unknown) (twenty-five (25) pages).
Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415 (three (3) pages).
Lelarge et al., Acute Unilateral Renal Failure and Contralateral Ureteral Obstruction, American Journal of Kidney Diseases, vol. XX, No. 3, Sep. 1992, pp. 286-288 (three (3) pages).
Doty et al., Effect of Increased Renal Venous Pressure on Renal Function, The Journal of Trauma: Injury, Infection and Critical Care, vol. 47, No. 6, Dec. 1999, pp. 1000-1003 (four (4) pages).
Edelson et al., Pharmacokinetics of Iohexol, a New Nonionic Radiocontrast Agent, in Humans, Journal of Pharmaceutical Sciences, vol. 73, No. 7, Jul. 1984, pp. 993-995 (three (3) pages).
Hvistendahl et al., Renal Hemodynamic Response to Gradated Ureter Obstruction in the Pig, Nephron 1996, 74:168-74 (seven (7) pages).
Pederson et al., Renal Water and Sodium Handling During Gradated Unilateral Ureter Obstruction, Scand J. Urol Nephrol, 2002, 36:163-72 (ten (10) pages).
Brezis et al., Hypoxia of the Renal Medulla—Its Implications for Disease, New England Journal of Medicine, vol. 322, No. 10, Mar. 9, 1995, pp. 647-655 (nine (9) pages).
Heyman et al., Pathophysiology of Radiocontrast Nephropathy: A Role for Medullary Hypoxia, Investigative Radiology, vol. 34, No. 11, Nov. 1999, p. 685-691 (seven (7) pages).
Office Action of the Canadian Intellectual Property Office for Canadian Patent Application No. 2,579,829 dated Jun. 13, 2008 (two (2) pages).
Written Opinion of the International Searching Authority for PCT Application No. PCT/US05/08948 dated Oct. 3, 2006 (five (5) pages).
Written Opinion of the International Searching Authority for PCT Application No. PCT/US2007/009683 dated Nov. 24, 2008 (eight (8) pages).
Written Opinion of the International Searching Authority for PCT Application No. PCT/US07/09685 dated Jul. 18, 2008 (twelve (12) pages).
Written Opinion of the International Searching Authority for PCT Application No. PCT/US07/09684 dated Jul. 21, 2008 (nine (9) pages).
Written Opinion of the International Searching Authority for PCT Application No. PCT/US08/07845 dated Sep. 17, 2008 (seven (7) pages).
Written Opinion of the International Searching Authority for PCT Application No. PCT/US08/07841 dated Sep. 18, 2008 (six (6) pages).
Written Opinion of the International Searching Authority for PCT Application No. PCT/US09/02739 dated Jun. 19, 2009 (six (6) pages).
Written Opinion of the International Searching Authority for PCT Application No. PCT/US2007/021791 dated May 8, 2008 (nine (9) pages).
Written Opinion of the International Searching Authority for PCT Application No. PCT/US 10/00137 dated Mar. 16, 2010 (eight (8) pages).
Written Opinion of ths International Searching Authority for PCT Application No. PCT/US2015/020196 dated Jun. 12, 2015, (five (5) pages).
Bart et al., "Ultrafiltration in Decompensated Heart Failure With Cardiorenal Syndrome", The New England Journal of Medicine, Dec. 13, 2012, pp. 2296-2304, Massachusetts Medical Society.
Briguori et al., "Renal Insufficiency After Contrast Media Administration Trial II (Remedial II): RenalGuard System in High-Risk Patients for Contrast-Induced Acute Kidney Injury", Circulation, Journal of the American Heart Association, Mar. 13, 2011, pp. 1-10.
Dorval et al., "Feasibility Study of the RenalGuard™ Balanced Hydration System: A Novel Strategy For the Prevention of Contrast-Induced Nephropathy in High Risk Patients", International Journal of Cardiology, 2011, pp. 1-5, Elsevier Ireland Ltd.
Felker et al., "Diuretic Strategies in Patients With Acute Decompensated Heart Failure", The New England Journal of Medicine, Mar. 3, 2011, vol. 364, No. 9, pp. 797-805.
Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, pp. e21-e181 and Correction sheet e424.
Marenzi et al., "Prevention of Contrast Nephropathy by Furosemide With matched Hydration". The MYTHOS (Induced Diuresis With Matched Hydration Compared to Standard Hydration for Contrast Induced Nephropathy Prevention) Trial, JACC: Cardiovascular Interventions, vol. 5, No. 1, 2012 The American College of Cardiology Foundation, pp. 90-97.
Mawer et al., "Value of Forced Diuresis in Acute Barbiturate Poisoning", British Medical Journal, Jun. 29, 1968, 2, pp. 790-793.
Paterna et al., "Changes in Brain Natriuretic Peptide Levels and Bioelectrical Impedance Measurements After Treatment With High-Dose Furosemide and Hypertonic Saline Solution Versus High-Dose Furosemide Alone in Refractory Congestive Heart Failure", Journal of the American College of Cardiology, 2005, vol. 45, No. 12, pp. 1997-2003.
Stevenson et al., "Editorial Comment, Torrent or Torment From The Tubules?", Challenge of the Cardiorenal Connections, Journal of the American College of Cardiology, vol. 45, No. 12, 2005, pp. 2004-2007.

FLUID THERAPY METHOD

RELATED APPLICATIONS

This application is a continuation of U.S. patent application Ser. No. 16/032,453 (U.S. Pat. No. 10,639,419), filed Jul. 11, 2018, which is a continuation of U.S. patent application Ser. No. 14/645,730, filed Mar. 12, 2015 and claims the benefit of U.S. Provisional Application Ser. No. 61/954,089 filed Mar. 17, 2014, all of which are incorporated by reference.

FIELD OF THE INVENTION

This invention relates to a patient hydration system and method wherein the rate of hydration fluid delivered to the patient is automatically adjusted based on the urine output and clinician settings in order to reach a clinician desired net fluid loss by the patient.

BACKGROUND OF THE INVENTION

Acute decompensated heart failure (ADHF) is the largest cause of hospitalization in the United States among patients 65 and older. See Lloyd-Jones D, Adams R, Carnethon M, et al. Heart disease and stroke statistics—2009 update: a report from the American Heart Association Statistics Committee and Stroke Statistics Subcommittee. Circulation 2009; 119(3):e21-e181 incorporated herein by this reference. These patients often enter the emergency room with significant volumes of excess fluid and a number of complications due to this excess fluid. Complications can include dyspnea, orthopnea, peripheral edema, and pulmonary edema.

Current treatment for these patients is to administer a number of doses of a diuretic to increate urination to enable the patient to lose the excess fluid. This therapy can take a number of days while the patient requires vigilant monitoring in an intensive care unit.

A recent study that attempted to determine the ideal diuretic dose for ADHF patients demonstrated how poorly patients fare with the current therapy. Across all treatment groups, 42% of patients enrolled in the trial died, were re-hospitalized, or had an emergency department visit within 60 days of treatment. See Felker G M, Lee K L, Bull D A, et al. Diuretic Strategies in Patients with Acute Decompensated Heart Failure (DOSE). The New England Journal of Medicine, 2011; 364(9):797-805 incorporated herein by this reference.

There are a number of factors that contribute to the poor prognosis of these patients. Patients with ADHF often have a number of co-morbidities, complicating their treatment and giving them a poor prognosis. These patients are often already taking a diuretic chronically, which lessens the impact of the diuretics when they are administered during their hospitalization. This also contributes to the fact that patient response to diuretics is unpredictable. Some patients may begin diuresis immediately after diuretic injection, others may require additional doses to induce diuresis.

A paradox of the ADHF patient involves the fact that while these patients may have 40 additional liters of fluid in their body, they may be intravascularly dehydrated. The extra fluid may be contained within the patient's cells and in the extra-cellular space ("third space"). The injection of diuretics then only causes fluid to be lost from the already depleted intravasculature. This can lead to a condition known as "diuretic resistance", wherein the patient's kidney attempts to retain the fluid lost after the initial doses of diuretic and fails to respond to increasing doses of diuretic. As fluid retention increases, the patient's urine output can drop to zero. Once the patient fails to respond to diuretics, treatment becomes very difficult. One of the ways ADHF kills patients is by retaining so much fluid that the fluid begins to build up in the patient's lungs, eventually causing pulmonary edema and eventually causing the lungs to fail. Diuretics are the most common method used to remove that excess fluid and prevent pulmonary edema. If diuretics fail to induce urine output due to diuretic resistance, the clinician loses an effective tool for protecting the patient from pulmonary edema.

The intravascular depletion caused by diuretic therapy can also reduce blood supply to the kidney, causing additional damage to the kidney.

Ultrafiltration therapy has been studied as a potential method for removing fluid from patients at risk of diuretic resistance. The therapy requires a pump that removes blood from the patient and passes the blood through a filter. The filter has small holes that allow fluid and electrolytes to be removed from the blood, but does not pass red blood cells or proteins. The blood is then returned to the body with some portion of the fluid and electrolytes removed. Ultrafiltration can be performed using a dialysis machine or a dedicated device, such as the Aquadex (Gambro, Brooklyn Park, Minn.).

While a number of studies have demonstrated that Ultrafiltration can effectively remove fluid from ADHF patients, one of the largest studies of the therapy to date has found that Ultrafiltration may lead to more kidney damage than diuretic therapy. See Bart B A, Goldsmith S R, Lee K L, et al. Ultrafiltration in Decompensated Heart Failure with Cardiorenal Syndrome, The New England Journal of Medicine, 2012; 367(24):2296-304 incorporated herein by this reference.

Hypertonic saline I.V. may be an effective in medical management of cerebral (brain) edema and elevated intracranial pressure (ICP). It is a critical component of perioperative care in neurosurgical practice. Traumatic brain injury (TBI), arterial infarction, venous hypertension/infarction, intracerebral hemorrhage (ICH), subarachnoid hemorrhage (SAH), tumor progression, and postoperative edema can all generate clinical situations in which ICP management is a critical determinant of patient outcomes. Use of hypertonic saline and other osmotic agents is among the most fundamental tools to control ICP. Recently several scientific papers taught the counterintuitive use of hypertonic saline to treat congestive heart failure (CHF or simply heart failure) patients with fluid overload resistive to diuretics. CHF patients retain salt and water to maintain blood pressure and their salt intake is severely limited by the traditional therapy paradigm.

Patema S, Di Pasquale P, Parrinello G, et al. in "Changes in brain natriuretic peptide levels and bioelectrical impedance measurements after treatment with high-dose furosemide and hypertonic saline solution versus high-dose of furosemide alone in refractory congestive heart failure: a double-blind study" (7 Am Coll Cardiol 2005; 45:1997-2003; further called Patena Paper) and Stevenson et al. in JACC Vol. 45, No. 12, 2005 Editorial Comment on the Patena Paper describe and comment on results from the randomized study of 94 patients hospitalized with clinical volume overload. The study suggests that the administration of sodium may paradoxically treat the sodium-retaining state. For acute diuresis, very high doses of loop diuretic furosemide (500 to 1,000 mg) were administered twice daily with either hypertonic saline or vehicle infusion concomitantly. Patients receiving hypertonic saline had greater volume loss and were discharged sooner, with better renal function and higher serum sodium.

According to Stevenson, the mechanisms by which in the acute phase of CHF the I.V. infusion of excess saline load facilitated diuresis are open to interpretation and complex. Unmistakably though, there was a larger amount of free water diuresis in the hypertonic saline group. This may relate in part to an acute osmotic effect of hypertonic saline to increase mobilization of extravascular fluid into the central circulation and renal circulation. Direct intratubular effects of sodium flooding may overwhelm the postdiuretic NaCl retention and over time may reduce the diuretic "braking" phenomenon by which fluid escaping past the ascending limb is captured downstream. Neurohormone levels may have been suppressed by hypertonic saline. Both increased intravascular volume and greater delivery of sodium to the distal tubule should inhibit the rennin-angiotensin-aldosterone system Inhibition of aldosterone release could explain the lower relative potassium excretion in the high sodium group, Reduction in angiotensin II levels could lead also to a decrease in antidiuretic hormone (ADH) vasopressin release despite temporary increase in serum osmolarity. There may also be a small contribution of increased intravascular volume to stimulation of the low-pressure and high-pressure baroreceptors that inhibit vasopressin release. Decreased levels of vasopressin could reduce the aquaporin channels through which water is reabsorbed, leading to the greater free water excretion observed. Reduced vasopressin also might also decrease compensatory over-expression of the sodium transporter in the ascending limb, which diminishes diuretic effect.

SUMMARY OF THE INVENTION

It is therefore the object of this invention to provide a fluid management system and a method for allowing the clinician to reliably achieve and maintain a high urine rate and then control the patient's fluid loss. A system in accordance with the invention makes the nurse's job easier. One method may treat patients with excess fluid. Another method is a fluid therapy method.

Featured is a method of treating a patient with excess fluid. The preferred method comprises setting a urine output rate desired threshold, setting a negative net fluid gain rate, and setting a desired total fluid loss goal. A diuretic is preferably administered to the patient to induce urine output. For a first therapy period after beginning diuretic administration, the urine output rate of the patient is driven to a higher level matching or exceeding the set urine output rate desired threshold. Such high urine output rates are achieved by automatically infusing fluid into the patient at rates which match or closely match the patient's urine output rates resulting in little or no total fluid loss. For a second therapy period after the set urine output rate desired threshold is reached, fluid loss is induced at the set negative net fluid gain rate by automatically decreasing the amount of fluid infused and infusing fluid at rates which are less than but a function of the patient's urine output rates until the desired total fluid loss goal is reached. A third therapy period may be involved wherein fluid is automatically infused at rates equal to or approximately equal to the patient's urine output rates after the desired total fluid loss goal is reached and until the end of therapy resulting in little or no total fluid loss during the third therapy period to prevent patient dehydration.

The method may further include administering a diuretic to the patient during the second therapy period. The diuretic may be administered automatically. Monitoring the urine output rates preferably includes collecting urine in a urine collection bag and weighing the urine collection bag as a function of time. Administering fluid to the patient preferably includes pumping fluid from a fluid bag into the patient using a fluid pump and automatically controlling the operation of the fluid pump. The method may include monitoring the operation of the fluid pump over time and/or weighing the fluid bag as a function of time to determine the rate of fluid infusion.

The infusion fluid may be saline or an osmotic solute. The method may further include automatically administering to the patient a bolus of fluid during therapy. The urine output rate desired threshold, the desired negative net gain rate, and the desired total fluid loss goal can be set via stored default values.

One fluid therapy method includes administering a diuretic to the patient to induce urine output and automatically monitoring the patient's urine output rates. For a first therapy period after administration of the diuretic, the urine output rate of the patient is driven to a higher level by automatically controlling an infusion pump to infuse fluid into the patient at rates which match or closely match the monitored patient's urine output rates until a set urine output rate threshold is reached resulting in little or no total fluid loss during the first therapy period. For a second therapy period after the set urine output rate threshold is reached, fluid loss is induced at a set negative net fluid gain rate by automatically controlling the infusion pump to decrease the amount of fluid infused and controlling the infusion pump to infuse fluid at rates which are less than but a function of the patient's urine output rates until a set desired total fluid loss goal is reached during the second therapy period. The method may further include a third therapy period wherein the infusion pump is controlled to infuse fluid at rates equal to or approximately equal to the patient's urine output rates after the set desired total fluid loss goal is reached and until the end of therapy resulting in little or no total fluid loss during the third therapy period to prevent patient hydration.

Also featured is a fluid therapy system comprising a console including an input for setting a urine output rate desired threshold and for setting a desired negative net fluid gain rate. The system further includes a urine output measuring subsystem and a fluid administration subsystem. A controller subsystem is responsive to the urine output measuring system and is configured to monitor the urine output rates of a patient. The controller subsystem is configured to control the fluid administration subsystem to automatically drive the urine output rate of the patient to a high level matching or exceeding the set urine output rate desired threshold by controlling the fluid administration subsystem to infuse fluid into the patient at rates that match or closely match the patient's urine output rates as measured by the urine output measuring subsystem resulting in little or no total fluid loss during a first therapy period. After the set urine output rate desired threshold is reached, the controller subsystem is configured to induce fluid loss at said set desired negative net fluid gain rate by again controlling the fluid administration subsystem to infuse fluid at rates which are now less than but a function of the patient's urine output rates as measured by the urine output measuring subsystem until the set desired total fluid loss goal it reached. The controller subsystem may be further configured to automatically control the fluid administration subsystem to infuse fluid at rates equal to or approximately equal to the patient's urine output rates as measured by the urine output measuring subsystem after the desired total fluid loss goal is reached and until the end of therapy resulting in little or no total fluid loss during a third therapy period to prevent patient dehydration. The system may further include a subsystem for automatically administering a diuretic to the patient before the first therapy period and, optionally, during the second therapy period.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features, and advantages will occur to those skilled in the art from the following description of a preferred embodiment and the accompanying drawings, in which.

DETAILED DESCRIPTION OF THE INVENTION

Figure 1:
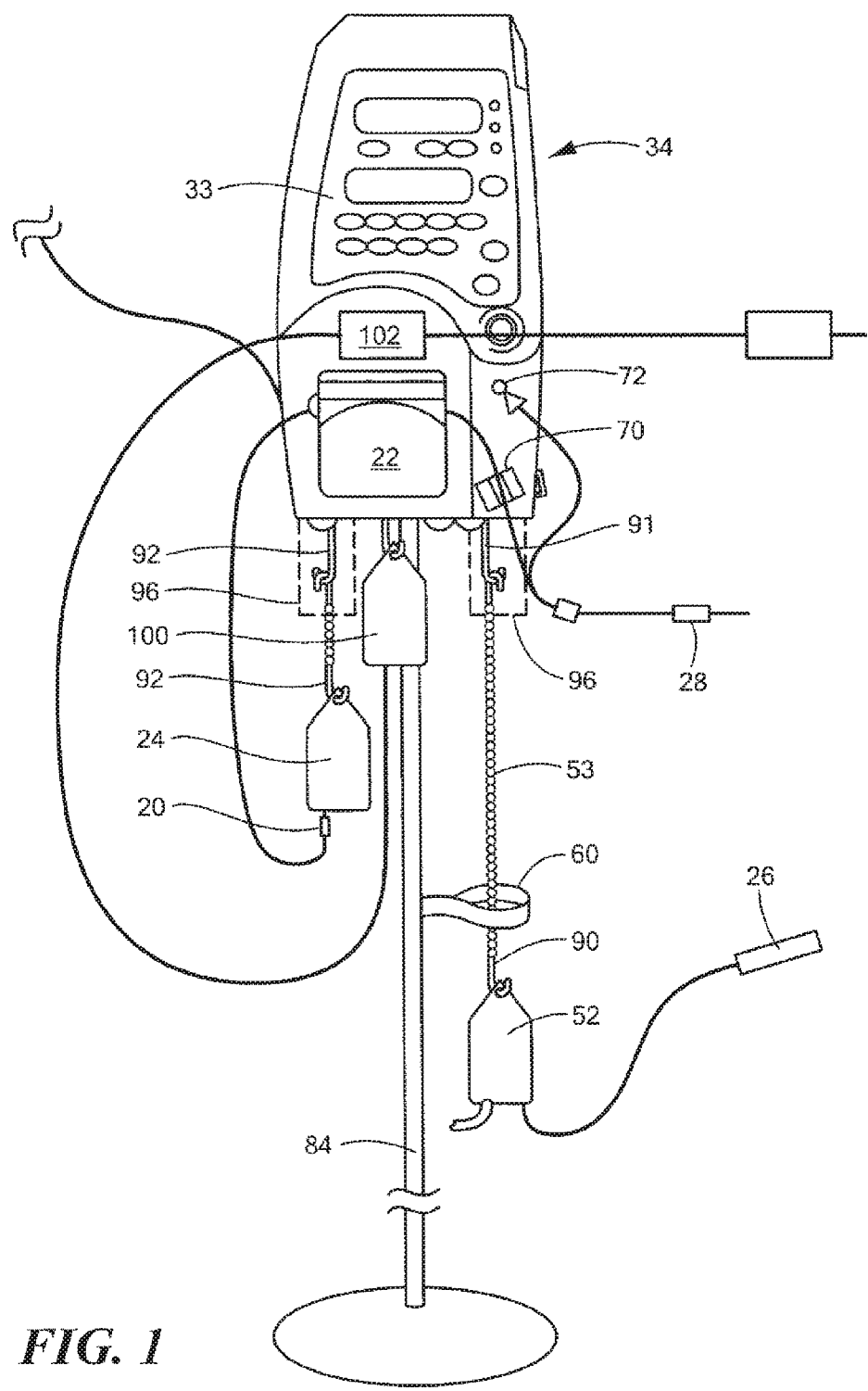
FIG. 1 is a view of an example of a system in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

In one example, the fluid management system comprises a urine collection system capable of measuring the patient's urine output, a controller that reads the output of the urine collection system and is capable of taking input from a user, and an infusion pump system that receives commands from the controller based on the urine collection readings and the user input. The urine collection system is connected to the patient via a catheter interface, such as a Foley catheter or a nephrostomy tube. The infusion pump system is connected to the patient via an infusion catheter.

Prior to beginning therapy, the clinician uses the fluid management system to set the urine rate they would like the patient to achieve before net fluid loss begins. The urine rate target can be as low as zero and as high a liter an hour or more. The clinician also sets the fluid loss profile the device should use once the patient achieves the target urine rate.

Additionally, the clinician can be given the option of setting a total loss fluid target. This is the total fluid loss the clinician would like the patient to achieve. The clinician is also given the option of setting an additional fluid infusion volume as a fluid challenge to help induce urine output.

The patient then receives an injection of a diuretic, such as Furosemide (Lasix), either in a bolus or via a continuous IV drip. The combination of Furosemide and matched replacement has been demonstrated in a number of trials to induce high urine rates. See Marenzi, Giancarlo, Prevention of Contrast Nephropathy by Furosemide with Matched Hydration: The MYTHOS Trial, JACC: Cardiovascular Interventions, Volume 5, Issue 1, January 2012, Pages 90-97; Dorval, Jean-Francois, Feasibility study of the RenalGuard™ balanced hydration system: A novel strategy for the prevention of contrast-induced nephropathy in high risk patients, International Journal of Cardiology. Int J Cardiol (2011), 10.1016/j.ijcard.2011.11.035 Dec. 29, 2011; and Briguori, Carlo, Renal Insufficiency After Contrast Media Administration Trial II (REMEDIAL H) Circulation, August 2011; Online ISSN: 1524-4539 all incorporated herein by this reference.

If target urine rate is not met within a user adjustable period of time, such as 30 minutes, the user is informed by an alert that the target urine rate has not been met. The alert recurs every interval until the target urine rate is met. Until the target urine rate is met, the fluid management system continues matched replacement.

When the target urine rate is met, an alert may be provided to the clinician to inform them that the target urine output rate has been reached and that the negative match profile we be initiated.

If clinically indicated, the clinician has the opportunity to indicate to the system that the negative match profile should begin as soon as therapy is initiated. This can be used in a patient who is already producing sufficient urine and does not require increased urine output to be induced.

Once the target urine rate is reached, then the set negative match profile automatically begins. A negative match profile can be as simple as match a set volume less than the patient's urine output every hour (i.e. −100 ml/hr). The user can set more complicated negative match profiles, such as match −50 ml/hr for the first hour, −75 ml/hr the second hour, −100 ml/hr the third hour and so on. The user can also select from pre-set profiles, such as a profile that slowly increases the negative match or one that aggressively increases the hourly negative match. The interval can also be more or less than an hour.

If the measured urine rate drops below the current set negative match rate or below another urine rate alert setting, the user is alerted. Alerts of low urine rate can occur directly via the fluid management system's screen or remotely through the hospital's network. Negative match profile continues until the clinician stops therapy. If the clinician set a total fluid loss target, the fluid management system stops the negative match profile when the patient reaches the total fluid loss target and resumes balanced hydration. An alert can be provided to the clinician to inform them that the fluid loss target has been met.

The hydration fluid could be any number of fluids, including but not limits to isotonic saline ("normal"), hypertonic saline, Ringer's Lactate, etc.

The fluid management system and method described enable the clinician to cause the patient to lose a set volume of fluid each hour while limiting the patient's hourly fluid loss. This enables the patient to maintain a brisk diuresis without becoming intravascularly dehydrated, preventing one of the major causes of diuretic resistance. See DOSE http://www.ncbi.nlm.nih.gov/m/pubmed/213664721 and CARRESS http://view.ncbi.nlm.nih.gov/pubmed/23131078 both incorporated herein by this reference.

One preferred example of a patient hydration system according to this invention includes unit 34, FIG. 1 typically mounted on IV pole 84. See U.S. Pat. Nos. 7,727,222 and 8,444,623 incorporated herein by this reference. Unit 34 has programmable controller electronics therein. There is an infusion subsystem including pump 22 responsive to source of infusion fluid 24 for infusing a patient with hydration fluid. Bag 100 may optionally include a diuretic infused into the patient by pump 102 controlled by the controller of the console 34. There is also a urine output measurement subsystem for determining the amount of urine output by the patient. In this particular example, source of infusion fluid bag 24 is hung on hook 92 and urine collection chamber or bag 52 is hung on hook 91 via chain 53 and hook 90. Unit 34 includes one or more weight scales such as an electronic strain gage or other means to periodically detect the weight of the collected urine in bag 52 and, if desired, the weight of the remaining hydration fluid in bag 24. Hooks 91 and 92 are connected to a system of levers which translates force to a scale such as a strain gage within unit 34. The strain gage converts force into an electronic signal that can be read by a controller. Suitable electronic devices for accurately measuring the weight of a suspended bag with urine are available from Strain Measurement Devices, 130 Research Parkway, Meriden, Conn., 06450. These devices include electronic and mechanical components necessary to accurately measure and monitor weight of containers with medical fluids such as one or two-liter plastic bags of collected urine. For example, the overload proof single point load cell model S300 and the model S215 load cell from Strain Measurement Devices are particularly suited for scales, weighing bottles or bags in medical instrumentation applications. Options and various specifications and mounting configurations of these devices are available. These low profile single point sensors are intended for limited space applications requiring accurate measurement of full-scale forces of 2, 4, and 12 pounds-force. They can be used with a rigidly mounted platform or to measure tensile or compressive forces. A 10,000.OMEGA. wheatstone bridge offers low power consumption for extended battery life in portable products. Other examples of gravimetric scales used to balance medical fluids using a controller controlling the rates of fluid flow from the pumps in response to the weight information can be found in U.S. Pat. Nos. 5,910,252; 4,132,644; 4,204,957; 4,923,598; and 4,728,433 incorporated herein by this reference.

It is understood that there are many ways known in the art of engineering to measure weight and convert it into computer inputs. Regardless of the implementation, the purpose of the weight measurement is to detect the increasing weight of the collected urine in the bag 52 and to adjust the rate of infusion or hydration based on the rate of urine flow by the patient by controlling infusion pump 22.

Unit 34 is also typically equipped with the user interface. The interface allows the user to set (dial in) the parameters of therapy such as the urine output rate desired threshold, a negative net gain rate, and/or a desired total fluid loss goal. Display indicators on the console show the set values and/or the current status of therapy: the elapsed time, the net fluid gain or loss, the amount of fluid infused, the amount of fluid loss, the loss rate, and/or the infusion rate, and the like.

The user interface may also include alarms. The alarms notify the user of therapy events such as an empty fluid bag or a full collection bag as detected by the weight scale. In one proposed embodiment, the urine is collected by gravity. If urine collection unexpectedly stops for any reason, the system will reduce and, if necessary, stop the IV infusion of fluid and alarm the user. Alternatively, the console can include the second (urine) pump similar to infusion pump 22. This configuration has an advantage of not depending on the bag height for drainage and the capability to automatically flush the catheter if it is occluded by temporarily reversing the pump flow direction.

Infusion pump 22 pumps infusion fluid from bag 24 into the patient and is controlled by the controller electronics within the unit which monitors the weight of the urine in urine collection bag 52.

Figure 3:
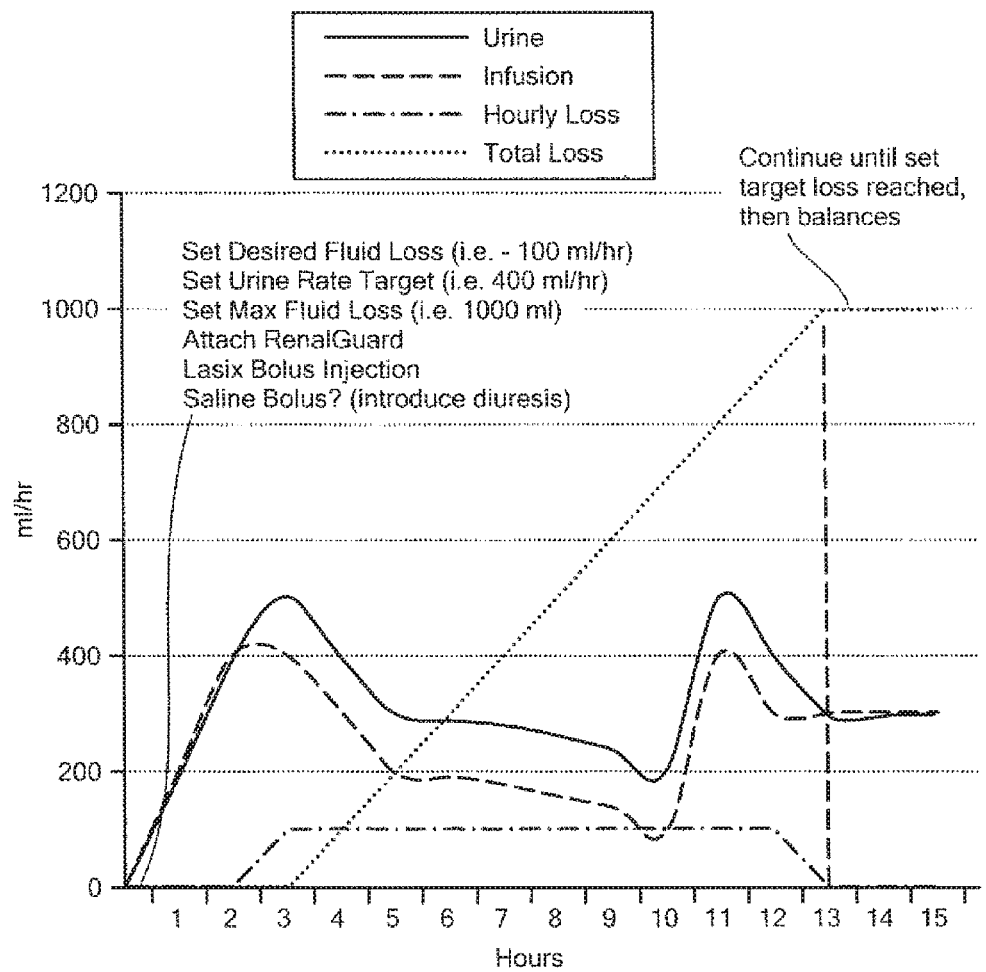
FIGS. 3-5 are examples of hydration profiles in accordance with methods of the invention and/or stored default values for the system of FIG. 1.
Figure 4:
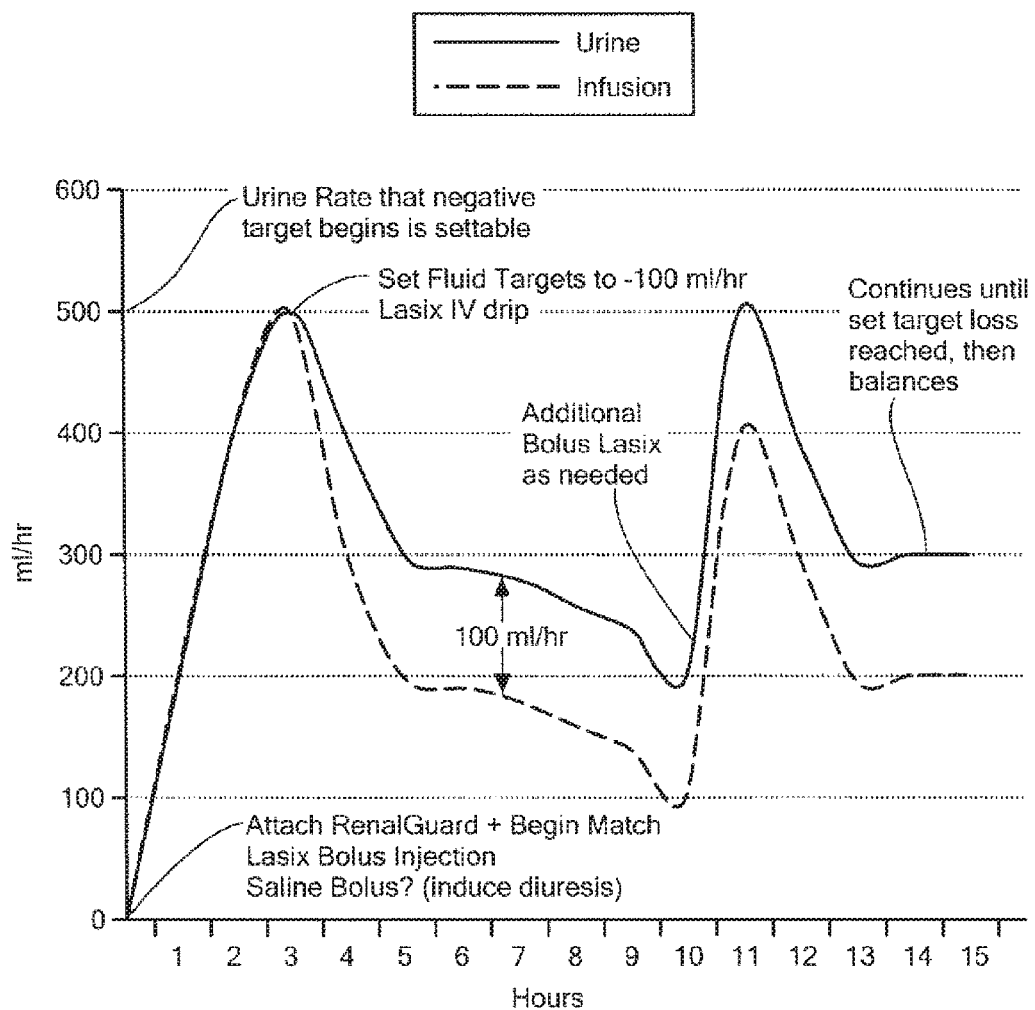
Figure 5:
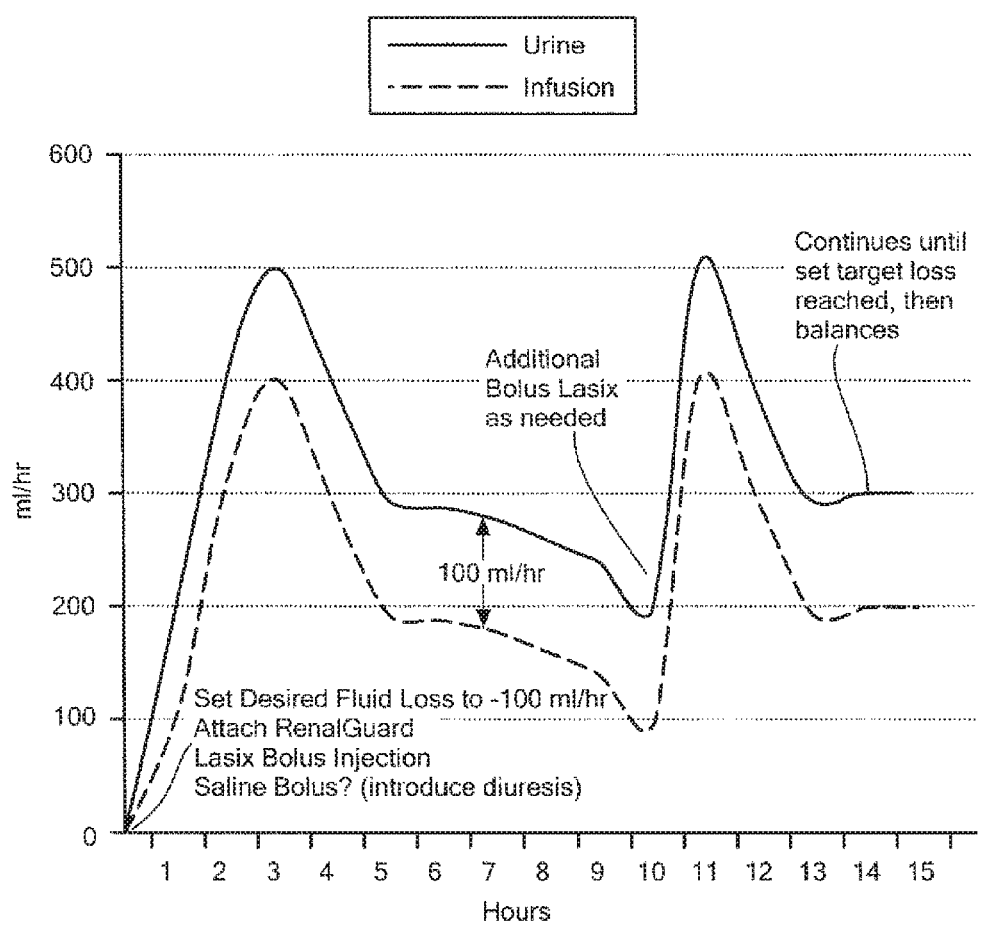

The electronic controller may also incorporate a more advanced feature allowing the physician to set a hydration profile selected from stored profiles depicted in FIGS. 3-5. See also U.S. application Ser. Nos. 11/408,391; 11/408,851; and Ser. No. 11/409,171 filed Apr. 21, 2006 which are incorporated herein by this reference.

In accordance with one example, the infusion set includes infusion bag "spike" connector 20 received in infusion fluid bag 24, luer connector 28 for receiving an IV needle, and tubing extending therebetween and placed within infusion pump 22. The urine collection set typically includes urine collection bag 52, Foley catheter connector 26 for connection to a Foley catheter, and tubing extending between the urine collection bag, and connector 26. The infusion set and the urine collection set are preferably placed together as a kit for the hydration unit in sealed bag for storage in a sterile fashion until ready for use. The integrated infusion set includes an IV bag spike, a Luer-to-Foley connector for priming, and a urine collection set includes an integrated urine bag.

The power requirements are typically 115/220 VAC, 60/50 Hz, 25 VA. An auxiliary ground post (potential equalization) for the device is on the rear of the case (not shown). An RS 232 port is also provided. When mounted on an I.V. Pole, the system requires an area of approximately 20.times.20 inches. Console 34 is placed on the pole so that the urine collection bag 52 is above floor level and not touching the floor or other equipment. Urine collection bag chain 53 is passed through motion restrictor ring 60 to prevent excessive swinging of the bag. Urine collection bag 52 is below the level of patient to facilitate urine drainage, and urine 52 and hydration fluid 24 bags are hanging freely on hooks 90 and 92, respectively, and not supported or impeded. Protection tubes 94 and 96 shown in phantom may be provided about hooks 91 and 92.

The system maintains hydration balance by measuring patient urine output and infusing hydration fluid (prescribed by physician) into the patient I.V. based on the patient's urine output and the clinician's settings. In addition to urine volume replacement, the system implements a user-set net fluid loss. The system also allows rapid infusion of a Bolus of fluid at the user request. The amount of Bolus can be selected by user and typically the bolus is infused over 30 minutes. Unit 34 typically includes a microcontroller device that has means for measuring urine output and the ability to infuse hydration fluid into the patient. The infusion set allows the console to pump fluid from a hydration fluid bag to the patient at a controlled rate. The disposable urine collection set collects the patient's urine to allow it to be measured accurately. Unit 34 is also equipped with an internal battery that can sustain operation in the event of power outage or during short periods of time, for example, when the patient is moved. Unit 34 may include roller pump 22, a user interface, two weighing scales (not shown), air detector 70, post-pump pressure sensor 72, an electrical connector for AC power, and mechanical interfaces for holding the set in place. Console 34 controls the rate at which fluid is infused and monitors urine volume by weight measurement.

In the subject invention, a controller e.g., a microprocessor or microcontroller or other circuitry (e.g., a comparator) in console 34, FIG. 1 controls hydration pump 22 to infuse the patient with hydration fluid based on the patient's urine output and keeps track of the hydration fluid injected in two ways to provide safety and redundancy. The preferred hydration fluid measurement subsystem includes, first, as discussed above, the weight of hydration fluid source 24, FIG. 1 which is monitored. Urine output is also monitored. In addition, the operation history of infusion pump 22 may be monitored by controller 100. The controller may store values representing both of these measurements in a memory such as a PROM and the controller is programmed to store the hydration fluid amounts administered via the hydration fluid measurement strain gauge, and the controller is also programmed to store the hydration fluid amount administered by monitoring of the hydration pump operation history.

One fluid therapy method includes setting a urine output rate desired threshold (e.g., 400 ml/hr). Such a desirably high urine output rate is uniquely achieved by first automatically balancing as shown in FIG. 3. One or more desired negative net gain rates are also set (e.g., −100 ml/hr). A desired total fluid loss goal is also set (e.g., 7004000 ml). The urine output of the patient is monitored and fluid is automatically administered to the patient at a rate equal to or approximately equal to the monitored urine output rate until the urine output rate reaches the set desired threshold. Thereafter, fluid is automatically administered to the patient at the set desired negative net gain rate until the total fluid loss goal is reached. Thereafter, until the end of therapy, fluid is automatically administered to the patient at a rate equal to or approximately equal to the monitored urine output rate to prevent hydration.

Monitoring the urine output rate may include collecting urine in a urine collection bag and weighing the urine collection bag as a function of time. Administering fluid to the patient may include pumping fluid from a fluid bag into the patient using a fluid pump. The method may include monitoring the operation of the fluid pump over time and/or weighing the fluid bag as a function of time to determine the rate of fluid infusion. A bolus of fluid may be administered during therapy. A diuretic may be administered during the therapy, e.g., at the start of therapy. The diuretic may be administered during the therapy when fluid is administered to the patient at a rate less than the monitored urine output rate according to the set desired negative net gain rate. The urine output rate desired threshold, the desired negative net gain rate, and/or the desired total fluid loss goal can be set via stored default values. Exemplary values are 400 ml/hr, −100 ml/hr, and 1000 ml, respectively. In some examples, the desired negative net gain changes during therapy as a function of time, e.g., −50 ml/hr for 1 hour, then −100 ml/hr for one hour, and then −150 ml/hr for another hour.

One fluid therapy method comprises setting one or more desired negative net gain rates, setting a desired total fluid loss goal, monitoring the urine output of a patient, administering diuretics to the patient, automatically administering the fluid to the patient at the set desired negative net gain rate until the total fluid loss goal is reached, and thereafter, until the end of therapy, automatically administering the fluid to the patient at a rate equal to or approximately equal to the monitored urine output rate.

Figure 2:
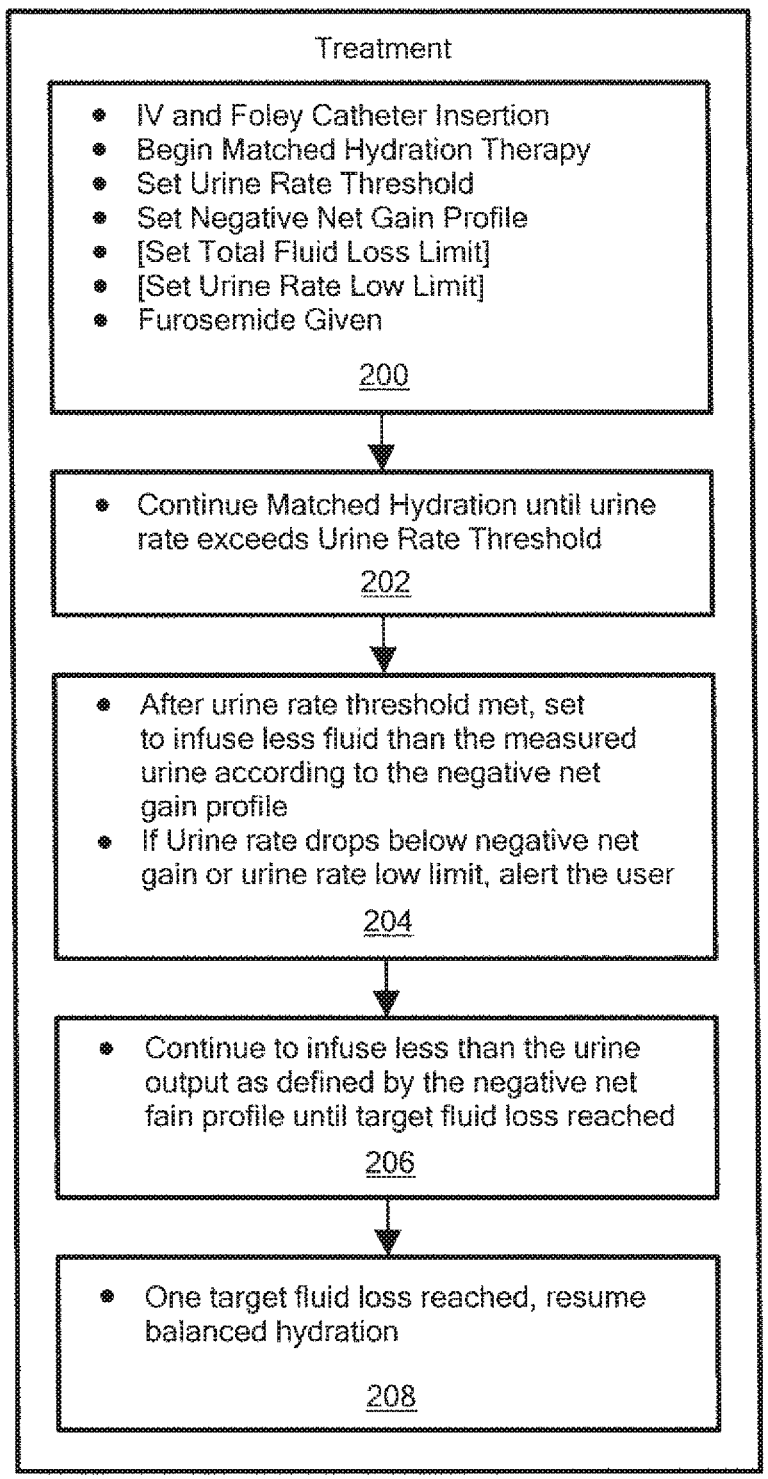
FIG. 2 is a flow chart depicting an example of the method of the invention and/or the primary steps associated with the programming of the controller in the system of FIG. 1.

A fluid therapy system in one example includes a console including an input section 33 for setting a urine output rate desired threshold, for a particular patient, for setting one or more desired negative net gain rates, and for setting a desired total fluid loss goal. The controller reads all three settings which may be stored in memory. See console 34, FIG. 1, step 200, FIG. 2. The system also includes a urine output measuring subsystem, a fluid administration subsystem, and a controller responsive to the urine output measuring subsystem and configured to monitor the urine output of a patient. The controller is programmed to control the fluid administration subsystem to automatically administer fluid to the patient at a rate equal to or approximately to the monitored urine output rate until the urine output rate reaches the set desired threshold, step 202. The controller monitors the urine output rate and is programmed to respond when the set urine output rate is reached. The controller is programmed, in response to the set urine output rate is reached to automatically thereafter administer fluid to the patient at the set desired negative net gain rate until the set total fluid loss goal is reached, steps 204, 206. The controller monitors the total fluid loss and when the goal is reached the controller is programmed to respond. The controller is programmed in response to the desired total fluid loss goal being reached to thereafter, until the end of therapy, automatically administer fluid to the patient at a rate equal to or approximately equal to the monitored urine output rate, step 208. The urine output measuring subsystem may include means for weighing a urine collection bag. The fluid administration subsystem may include a fluid pump and means for weighing a fluid bag connected to the fluid pump.

Featured is a method of treating a patient with excess fluid. A urine output rate desired threshold, and/or a negative net fluid gain rate, a desired total fluid loss goal are set in unit 34, FIG. 1. A diuretic is administered (manually or automatically) to the patient to induce urine output at hour 0 of therapy, FIG. 3. For a first therapy period after administration of the diuretic, the urine output rate of the patient is driven to a higher level matching or exceeding the set urine output rate (e.g., over 400 ml/hr) desired threshold by automatically infusing fluid into the patient at rates which match or closely match the patient's urine output rates resulting in little or no total fluid loss as shown in hours 0-2 of therapy in FIG. 3. For a second therapy period after the set urine output rate desired threshold is reached, fluid loss is induced at the set negative net fluid gain rate by automatically decreasing the amount of fluid infused and infusing fluid at rates which are less than but a function of the patient's urine output rates until the set desired total fluid loss goal is reached as shown in hours 2-13 of therapy in FIG. 3. Optionally, a diuretic may again be administered (manually or automatically) during this second therapy period as shown at hour 10. In the third therapy period, fluid is automatically infused at rates equal to or approximately equal to the patient's urine output rates after the desired total fluid loss goal is reached and until the end of therapy resulting in little or no total fluid loss during the third therapy period to prevent patient dehydration as shown in hours 13-15 of the therapy in FIG. 3.

Monitoring the urine output rates may include collecting urine in a urine collection bag 52, FIG. 1 and weighing the urine collection bag as a function of time. Administering fluid to the patient may include pumping fluid from a fluid bag 24 into the patient using a fluid pump 22 and automatically controlling the operation of the fluid pump. The controller may include software instructions for monitoring the operation of the fluid pump over time and/or weighing the fluid bag as a function of time to determine the rate of fluid infusion. See for example, U.S. Pat. Nos. 7,727,222 and 8,444,623 incorporated herein by this reference. The infusion fluid may be saline or an osmotic solute. The urine output rate desired threshold, the desired negative net gain rate, and the desired total fluid loss goal may also be set via stored default values.

The clinical efficacy of this therapy has been established based on three sets of data.

The ability of the system to induce high urine rates by measuring a patient's urine output and infusing a volume of hydration fluid has been well established. This has been demonstrated in hundreds of patients in studies to evaluate the ability of this system, combined with a small furosemide dose, to prevent contrast-induced acute kidney injury (MYTHOS, REMEDIAL II, Dorval). In Dorval, the average urine rate was 620 ml/hr+/−400 ml/hr, MYTHOS 760 ml/hr, and REMEDIAL II 352 ml/hr+/−131 ml/hr. These results have been replicated in thousands of cases where the system has been used in clinical practice around the world.

The ability of this system to be used safely in patients with acute decompensated heart failure was first established by Dr. Albrecht Roemer and his team at St. Josefs-Hospital, Wiesbaden, Germany. They used the system experimentally to manage the fluid balance of a patient described to have "severely depressed EF" with a rising serum creatinine level, which indicated that the patient was developing acute kidney injury. Their goal was to maintain the patient's intravascular fluid volume. They gave the patient a bolus of 500 ml then second bolus of 500 ml. Only then did they give a furosemide bolus. Urine output exceeded 300 ml/hr and dropped to between 200-250 ml/hr, but remained within this range. The patient did develop very mild edema, but it was not severe, and the patient tolerated the therapy well. The patient's serum creatinine level dropped, indicating resolution of the patient's acute kidney injury and the patient recovered. This experience established that this system could be used in patients with severely depressed ejection fraction who are at very high risk of developing fluid overload and induce the high urine rates that have shown to be protective of the kidney while not causing fluid overload and severe pulmonary edema.

The final support for this therapy comes from the clinical experimental experience of Professor Shlomi Matetzky of Sheba Medical Center. Prof. Matetzky and his team have used the system to treat 8 patients at high risk of developing pulmonary edema.

In patients with chronic heart failure that presented with acute heart failure and renal failure (or the risk of renal failure), their clinical goal was to improve cardiac function, which in turn improves renal function by improving renal blood flow. In these patients, they would set the desired fluid balance to −50 ml/hr and give the patient Furosemide to drive urine output. In these patients they were able to take fluid off in a controlled manner without the patient developing acute kidney injury or becoming dehydrated or developing pulmonary edema.

They also used the concept of first inducing urine output first by providing balanced or even positive fluid balance and once the urine output has reached the desired level, setting the desired fluid balance negative to allow the patient to slowly lose fluid. This has been particularly effective in patients who presented with intravascular dehydration and fluid overload.

All patients treated using the system in Prof. Matetzky's unit have seen improvements in renal function and none have developed pulmonary edema.

These three sets of data demonstrate that the system claimed herein has the ability to safely be used in patients with fluid overload or who are at high risk of developing fluid overload and can be used to induce high urine rates and help those patients slowly and safely lose excess fluid.

Regardless of its mechanisms of action, hypertonic saline therapy could be an additional useful clinical tool to force diuresis and resolve fluid overload in CHF patients. It is not currently used in routine clinical practice since many concerns are raised in regard to safety and nursing labor involved in the implementation of such therapy. Fluid retention in some patients results from low sodium content of blood plasma and can be overcome by the I.V. infusion of hypertonic saline. Sodium is a vital electrolyte. Its excess or deficit in blood serum can cause hypematremia or hyponatremia that can result in abnormal heart rhythm, coma, seizures, and death. Administration of an effective therapy with hypertonic saline requires careful monitoring and tight controls. A system and a method have been developed to reduce fluid overload and edema and force diuresis in patients with heart failure and other conditions leading to fluid retention, that do not respond to conventional drug therapy. The system and method provides controlled infusion of an osmotic agent (i.e. hypertonic saline) into the patient's I.V. that is safe and easy to use.

A novel patient infusion, monitoring and control system has been developed that, in one embodiment, comprises:

A. A source of a solution of a blood compatible osmotic I.V. infusible agent such as hypertonic saline, B. An infusion pump and an I.V. set for controlled delivery of the agent to the patient, C. A biofeedback sensors connected to the patient that allow monitoring and guiding of the therapy, D. A microprocessor based controller responsive to the biofeedback signals and is configured to adjust the infusion rate of the pump based on the output of the biofeedback sensors controlling the infusion of the osmotic agent.

In an embodiment that targets therapy of CHF patients, the biofeedback component is comprised of a urine volume monitoring device and a sensor monitoring sodium concentration in urine. The infusion pump is designed for accurate volume delivery. The concentration of sodium in the infusion fluid is known. This allows the controller to calculate the amount of sodium and water delivered to the patient (the "ins"). Urine monitoring measures the amount of water and sodium excreted by the patient (the "outs"). The system balances (the "ins" and "outs") the total sodium amount in the patient's body water and achieves the desired sodium concentration in plasma. Optionally gradual controlled increase of sodium concentration in serum can be achieved by: a) removal of excess free water in urine, and b) net positive ("ins" over "outs") addition of small amounts of sodium gradually over hours and days of therapy. As a result, free water excretion is increased, while sodium concentration in blood is maintained within the desired and safe range or increased gradually and safely as desired.

It is understood that the osmotic agent can be a blood compatible small molecule solute other than sodium, such as for example urea. It is preferred that the osmotic agent is normally present in the blood plasma and interstitial water and is excreted by kidneys. It is also understood that the biofeedback may be a physiologic parameter indicative of total or local (in a compartment) body fluid volume such as intracranial pressure (ICP). While the placement of an ICP monitor is invasive, the benefits of ICP monitoring are felt to offset this factor in ICU patients with severe brain trauma. Percutaneous devices (e.g., ventriculostomy catheters) for use in monitoring ICP are commercially available in a variety of styles and from a number of sources. The biofeedback also may be a direct measurement of an osmotic agent and particularly sodium concentration in blood performed using blood chemistry sensors such as, for example, an i-STAT Device manufactured by Abbot Health Care.

In one example, the control system includes a measuring or monitoring sensor as part of or responsive to sodium in the urine collection system and configured to determine the urine output from the patient and a controller responsive to the meter. Typically, the urine collection system includes a urinary catheter connected to the urine collection chamber. In one embodiment, the meter is a weighing mechanism for weighing urine in the collection chamber and outputting a value corresponding to the weight of the urine to the controller. The controller and the weighing mechanism can be separate components or the controller and the weighing mechanism may be integrated. Other types of meters which measure urine output (e.g., volume or flow rate), however, are within the scope of this invention.

Typically, the controller is programmed to determine the rate of change of the urine weight, the rate of change of the urine sodium concentration, to calculate a desired infusion rate based on the rate of change of the urine weight, and to adjust the infusion rate of the infusion pump based on the calculated desired infusion rate to replace sodium lost in urine in a more concentrated solution than urine sodium concentration. As a result net loss of free water is achieved and blood serum sodium concentration is increased, which is the desired goal of the therapy.

It is preferred that the controller subsystem includes a user interface which is configured to allow the user to set a desired serum concentration level achieved in a predetermined time period. The user interface may also include a display indicating the net water and sodium gain or loss, and a display indicating the elapsed time. The user interface can be configured to allow the user to set duration of replacement and to allow the user to set a desired net fluid balance in hourly steps or continuous ramp rate. The control subsystem may also include an alarm subsystem including an air detector. The control subsystem is responsive to the air detector and configured to stop the infusion pump if air exceeding a specified amount is detected. The alarm subsystem may be responsive to the urine collection system and configured to provide an indication when the urine collection system has reached its capacity. The alarm subsystem may also be responsive to the infusion system and configured to provide an indication when the infusion subsystem is low on infusion fluid.

The system may further include a diuretic administration system and/or a blood chemistry sensor responsive to changes of blood sodium concentration. The system may further include a biosensor directly responding to intracranial pressure or the interstitial fluid pressure in a body compartment where edema is present.

A method of removing excess interstitial fluid from the patient with fluid overload and edema in accordance with this invention includes the steps of:

A. Monitoring a biological sensor responsive to a physiologic variable;

B. Controlling the infusion pump based on the said parameter; and

C. Infusing osmotic agent into the patient's blood.

The step of monitoring may comprise measuring the urine output volume and composition. The step of measuring the urine output may further include weighing the urine output by the patient. Typically, the step of adjusting the infusion rate includes determining the rate of excretion of sodium in the urine of the urine output by the patient, calculating a desired infusion rate based on the rate of change of the urine sodium, and adjusting the infusion rate based on the calculated desired infusion rate.

The method may further include the steps of setting a goal (desired or target value) net sodium balance level (net loss or gain) to be achieved by the control algorithm in a predetermined time period, displaying the net fluid and sodium gain or loss, displaying the elapsed time, setting a duration of therapy of the patient, and/or detecting air during the step of infusing the patient with the fluid containing an osmotic agent and automatically stopping infusion if air exceeding a specified amount if detected.

Presumably, as a result, diuresis of a patient is achieved by removal of free water while increasing delivery of sodium to the kidney. Other benefits to the patient, such as vasodilatation, improved heart function, reduced hormone levels and improved kidney function can be expected. Typically, for the proposed method, sodium concentration in urine is substantially lower than in the infused fluid. While the same absolute amount of sodium, thus returned to the patient, may be the same, negative net balance (loss) of water can be achieved. For example, urine Na concentration can be 100 mEq/L and the infusion fluid sodium concentration can be 300 mEq/L. A 1 liter of fluid lost in urine can be replaced with ⅓ liter of I.V. fluid to achieve zero net sodium balance. As a result, theoretically, ⅔ liter of free water will be lost by the patient and no net loss of sodium will occur. Concentration of sodium in blood plasma will increase in proportion to the reduction of total body water. This example does not account for patient's drinking or for the water lost by evaporation.

In some embodiments, bag 24, FIG. 1 is filled with an osmotic agent infused during all three therapy time periods shown in FIG. 3. In other embodiments, an osmotic agent is only infused during the second therapy period. In some embodiments, the controller of unit 34, FIG. 1 is responsive to a biofeedback sensor associated with urine bag 52 and controls the infusion of the osmotic agent as described above. In one example, when the sensor detects a sodium concentration in the patient's urine or blood less than a threshold, the infusion pump is controlled to automatically infuse additional amounts of the osmotic agent until the sodium concentration exceeds the threshold.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

The below pseudo-code provides an implementation of the fluid management software operable on controller 34:

```
Reach Threshold then Begin Net Negative Algorithm:
ThresholdThenNegative( )
{
        UrineOutputThresholdSetting = GetUrineThresholdSetting( )
        FluidChallengeSetting = GetFluidChallengeSetting( )
        DesiredNetGainProfile = GetNetGainProfileSetting( )
        TotalUrineOutput = ReadUrineOutput( )
        UrineOutputRate = CalculateUrineRate(TotalUrineOutput)
        TotalFluidinput = ReadFluidinput( )
        //until urine output exceeds threshold, balance
        LastUrineOutputAlertTime = Now( )
        While ( UrineOutputRate < UrineOutputThresholdSetting)
        {
            //set fluid balance to 0 plus any user set fluid challenge
            DesiredFluidBalance =0+FluidChallengeSetting
            InfusionPumpRate=GetInfusionPumpRate(TotalUrineOutput,
                TotalFluidInput, DesiredFluidBalance)
            TotalUrineOutput = ReadUrineOutput( )
            UrineOutputRate = CalculateUrineRate(TotalUrineOutput)
            TotalFluidInput = ReadFluidInput( )
            //if target urine rate not met for specified time, tell user
            If(ElapsedTime(LastUrineOutputAlertTime) > AlertInterval)
                {
                    ReportAlert(UrineOutputThresholdNotMet)
                    LastUrineOutputAlertTime =Now( ) //reset time
                }
        }
        DisplayUserMessage(UrineThresholdMet)
        //once urine output reaches threshold, begin Desire negative net
gain profile until user stops it
        While (CheckUserExit( )= FALSE)
    {
        DesiredFluidBalance = GetDesiredNetGain
        (DesiredNetGainProfile)
        InfusionPumpRate = GetInfusionPumpRate(TotalUrineOutput,
        TotalFluidInput, DesiredFluidBalance)
        TotalUrineOutput = ReadUrineOutput( )
        UrineOutputRate = CalculateUrineRate(TotalUrineOutput)
        TotalFluidInput = ReadFluidInput( )
    }
        Return;
}
Reach Threshold then Begin Net Negative Algorithm until total loss goal
reached:
ThresholdThenNegativeUntilGoal( )
{
        UrineOutputThresholdSetting = GetUrineThresholdSetting( )
        DesiredNetGainProfile = GetNetGainProfileSetting( )
        FluidChallengeSetting = GetFluidChallengeSetting( )
        FluidLossGoalSetting = GetFluidLossGoalSetting( )
        TotalUrineOutput = ReadUrineOutput( )
        UrineOutputRate = CalculateUrineRate(TotalUrineOutput)
        TotalFluidInput = ReadFluidInput( )
        LastUrineOutputAlertTime =Now( ) //reset time
        //until urine output exceeds threshold, balance
        While (UrineOutputRate <UrineOutputThresholdSetting )
        {
            //set fluid balance to 0 plus any user set fluid challenge
            DesiredFluidBalance = 0+FluidChallengeSetting
            InfusionPumpRate =
                GetInfusionPumpRate(TotalUrineOutput,
                TotalFluidInput, DesiredFluidBalance)
            TotalUrineOutput = ReadUrineOutput( )
            UrineOutputRate = CalculateUrineRate(TotalUrineOutput)
            TotalFluidInput = ReadFluidInput( )
            //if target urine rate not met for specified time, tell user
            If(ElapsedTime(LastUrineOutputAlertTime) >
            AlertInterval)
                {
                    ReportAlert(UrineOutputThresholdNotMet)
                    LastUrineOutputAlertTime =Now( ) //reset time
                }
        }
        DisplayUserMessage(UrineThresho ldMet)
        //once urine output reaches threshold, begin Desire negative
net gain profile until user stops it
        TotalFluidLoss = TotalFluidInput- TotalUrineOutput
        //continue until fluid loss goal is reached
        While (CheckFluidGoalReached(FluidLossGoalSetting,
   TotalFluidLoss) = FALSE)
        {
            DesiredFluidBalance = GetDesiredNetGain(
            DesiredNetGainProfile) InfusionPumpRate =
            GetInfusionPumpRate(TotalUrineOutput,
            TotalFluidInput, DesiredFluidBalance)
            TotalUrineOutput = ReadUrineOutput( )
            UrineOutputRate = CalculateUrineRate(TotalUrineOutput)
            TotalFluidInput = ReadFluidInput( )
            TotalFluidLoss = TotalFluidinput- TotalUrineOutput
        }
        //once target reached, continue balancing
        DisplayUserMessage(FluidLossGoalMet)
        While (CheckUserExit( )= FALSE)
        {
            DesiredFluidBalance = 0
            InfusionPumpRate =
                GetInfusionPumpRate(TotalUrineOutput, TotalFluidInput,
                DesiredFluidBalance)
            TotalUrineOutput = ReadUrineOutput( )
            UrineOutputRate = CalculateUrineRate(TotalUrineOutput)
            TotalFluidInput = ReadFluidInput( )
        }
        Return;
}
Reach Threshold then Begin Net Negative Algorithm until total loss goal
reached with diuretic infusion:
ThresholdThenNegativeUntilGoalWithDiureticinfusion( )
{
        UrineOutputThresholdSetting = GetUrineThresholdSetting( )
        DesiredNetGainProfile = GetNetGainProfileSetting( )
        FluidChallengeSetting = GetFluidChallengeSetting( )
        FluidLossGoalSetting = GetFluidLossGoalSetting( )
        DiureticDosingProfileSetting = GetDiureticDosingSetting( )
//getdosing and logic for dosing (i.e. if urine rate< X ml/hr give Y dose
        TotalUrineOutput = ReadUrineOutput( )
        UrineOutputRate = CalculateUrineRate(TotalUrineOutput)
        TotalFluidInput = ReadFluidJnput( )
        LastUrineOutputAlertTime =Now( ) //reset time
        //until urine output exceeds threshold, balance
        While ( UrineOutputRate <UrineOutputThresholdSetting )
        {
            //set fluid balance to 0 plus any user set fluid challenge
            DesiredFluidBalance=0+FluidChallengeSetting
            InfusionPumpRate =
                GetInfusionPumpRate(TotalUrineOutput,
                TotalFluidJnput, DesiredFluidBalance)
            TotalUrineOutput=ReadUrineOutput( )
            UrineOutputRate = CalculateUrineRate(TotalUrineOutput)
            TotalFluidInput = ReadFluidInput( )
            ProcessDiureticInfusion(U rineRate,
            DiureticDosingProfileSetting)
            //if target urine rate not met for specified time, tell user
            If (ElapsedTime(LastUrineOutputAlertTime) > AlertInterval)
                {
                    ReportAlert(UrineOutputThresholdNotMet)
                    LastUrineOutputAlertTime =Now( ) //reset time
                }
        }
        DisplayUserMessage(UrineThresholdMet)
        //once urine output reaches threshold, begin Desire negative net
gain rofile until user stops it
        TotalFluidLoss = TotalFluidinput- TotalUrineOutput
        //continue until fluid loss goal is reached
        While (CheckFluidGoalReached(FluidLossGoalSetting,
   TotalFluidLoss) = FALSE)
        {
            DesiredFluidBalance =
                GetDesiredNetGain(DesiredNetGainProfile)
            InfusionPumpRate=GetinfusionPumpRate(TotalUrineOutput,
                TotalFluidinput, DesiredFluidBalance)
            TotalUrineOutput = ReadUrineOutput( )
            UrineOutputRate = CalculateUrineRate(TotalUrineOutput)
            TotalFluidinput = ReadFluidinput( )
            TotalFluidLoss = TotalFluidInput- TotalUrineOutput
            ProcessDiureticinfusion(UrineRate,
            DiureticDosingProfileSetting)
        }
```

```
            //once target reached, continue balancing
            DisplayUserMessage(FluidLossGoalMet)
            While (CheckUserExit( )= FALSE)
            {
                DesiredFluidBalance = 0
                InfusionPumpRate =
                    GetinfusionPumpRate(TotalUrineOutput,
                    TotalFluidInput, DesiredFluidBalance)
                TotalUrineOutput = ReadUrineOutput( )
                UrineOutputRate = CalculateUrineRate(TotalUrineOutput)
                TotalFluidInput = ReadFluidInput( )
            }
            Return;
}
ProcessDiureticInfusion( UrineRate, DiureticDosingProfileSetting)
{
        //find dose setting based on urine rate
        DiureticDoseProfile=DiureticDosingProfileSetting [UrineRate]
        If (DiureticDoseProfile.Rate > 0)
        {
            If(DiureticDoseProfile.InfusionType =Continuous)
//continuous or interval
            {
                SetDiureticPump (DiureticDosePro file.Rate)
            }
            Else //dose is at interval
            {
                If(DiureticDoseProfile.lnterval =Now( )) //if interval,
                and interval
expired, give diuretic
                SetDiureticPump (DiureticDoseProfile.Rate)
            }
        }
}
```

The invention claimed is:

1. A fluid therapy method comprising:
  automatically measuring urine output of a patient;
  automatically infusing a fluid intervascularly into the patient;
  automatically controlling the infusion of the fluid to achieve a zero or positive fluid balance during a first period while a patient is being dosed with a diuretic and while the measured urine output of the patient is below a first threshold urine output level; and
  after the measured urine output exceeds the first threshold urine output level, the automatic controlling of the infusion includes adjusting the infusion of the fluid to achieve a negative fluid balance during a second period following the first period.

2. The method of claim 1, wherein the adjustment the infusion of the fluid includes reducing a rate of the infusion to less than a current rate of the measured urine output.

3. The method of claim 1, further comprising inputting the first threshold urine output level to a computer which performs the automatic measuring of the urine, and the automatic controlling of the infusion of the fluid.

4. The method of claim 1 in which the fluid is saline or an osmotic solute.

5. The method of claim 1 in which the fluid is hypertonic saline.

6. The method of claim 1, wherein the first threshold urine output level is a first threshold rate of urine output or a first threshold volume of urine output.

7. The method of claim 1 further including administering to the patient a diuretic while the fluid is infused and after the measured urine output exceeds a first threshold urine output level.

8. The method of claim 1 wherein the first threshold urine output level is a urine output rate of at least a liter an hour.

9. The method of claim 1, in which the negative fluid balance is a positive difference between a current measured urine output level and a current infusion level of the fluid.

10. The method of claim 1, in which the negative fluid balance is a positive difference between a current urine output rate and a current infusion rate of the fluid.

11. The method of claim 1, wherein the negative fluid balance becomes progressively greater during the second period.

12. The method of claim 10, wherein the negative fluid balance, during the second period, is initially 50 ml/hr and is later increased to at least 75 ml/hr.

13. The method of claim 1, wherein the first threshold urine output is 400 ml/hr.

14. The method of claim 10, wherein rate of the infusion of the fluid to achieve the negative fluid balance is determined as function of the measured urine output.

15. A method of treating a patient having excess fluid, the method comprising:
  administering a diuretic to the patient to induce urine output by the patient;
  for a first therapy period after beginning the diuretic administration, a controller infuses a fluid intravenously into the patient at a level matching or exceeding a current urine output level until the current urine output level reaches a first threshold urine output level; and
  for a second therapy period after the urine output reaches the first threshold urine output level, the controller induces fluid loss in the patient by adjusting the infusion of the fluid to a level below the current urine output level.

16. The method of claim 15, in which the negative fluid balance is a positive difference between the current urine output and a current infusion level of the fluid.

17. The method of claim 15, wherein the negative fluid balance becomes progressively greater during the second period.

18. The method of claim 15, wherein the negative fluid balance, during the second period, is initially 50 ml/hr and is later increased to at least 75 ml/hr.

19. The method of claim 15, wherein the first threshold urine output level is a first threshold rate of urine output or a first threshold volume of urine output.

* * * * *